(12) United States Patent
Nicholls et al.

(10) Patent No.: US 8,460,330 B2
(45) Date of Patent: Jun. 11, 2013

(54) LANCING DEVICES

(75) Inventors: Clive Nicholls, Buckinghamshire (GB); Robert Michael Wozencroft, Surrey (GB)

(73) Assignee: Owen Mumford Limited, Oxford ( * ) Notice: Subject to any disclaimer, the term of this patent is extended or adjusted under 35 U.S.C. 154(b) by 140 days.

(21) Appl. No.: 12/673,364

(22) PCT Filed: Aug. 14, 2008

(86) PCT No.: PCT/GB2008/002749
§ 371 (c)(1),
(2), (4) Date: Jun. 1, 2010

(87) PCT Pub. No.: WO2009/022138
PCT Pub. Date: Feb. 19, 2009

(65) Prior Publication Data
US 2012/0010641 A1    Jan. 12, 2012

(30) Foreign Application Priority Data
Aug. 14, 2007   (GB) .................................... 0715800.9

(51) Int. Cl.
*A61B 17/32*    (2006.01)
(52) U.S. Cl.
USPC ....................................................... 606/182
(58) Field of Classification Search
USPC ............................................... 606/181, 182
See application file for complete search history.

(56) References Cited

U.S. PATENT DOCUMENTS

| | | | | |
|---|---|---|---|---|
| 7,708,701 B2 * | 5/2010 | Boecker et al. | ............... | 600/583 |
| 8,246,645 B2 | 8/2012 | Yoritaka et al. | | |
| 2006/0241669 A1 * | 10/2006 | Stout et al. | ..................... | 606/182 |
| 2006/0264996 A1 * | 11/2006 | LeVaughn et al. | ............ | 606/181 |
| 2010/0049234 A1 * | 2/2010 | Kitamura et al. | ............. | 606/182 |
| 2010/0130997 A1 * | 5/2010 | LeVaughn et al. | ............ | 606/172 |

FOREIGN PATENT DOCUMENTS

| | | |
|---|---|---|
| EP | 1806095 A1 | 7/2007 |
| GB | 2 434 540 A | 8/2007 |
| WO | WO 03/071940 | 9/2003 |
| WO | 2005018454 A2 | 3/2005 |
| WO | WO 2005/018430 A2 | 3/2005 |
| WO | WO 2005/018711 A2 | 3/2005 |
| WO | WO 2005018430 A2 * | 3/2005 |
| WO | WO 2006/128752 A2 | 12/2006 |
| WO | 2007037207 A1 | 4/2007 |

OTHER PUBLICATIONS

International Search Report, dated Nov. 28, 2008, from corresponding PCT application.
European Office Action dated Dec. 21, 2011, from corresponding EP application.
GB Search Report, dated Nov. 9, 2007, from corresponding GB application.

* cited by examiner

*Primary Examiner* — Ryan Severson
*Assistant Examiner* — Julie A Szpira
(74) *Attorney, Agent, or Firm* — Young & Thompson

(57) ABSTRACT

A lancing device includes a main housing 28 having in the forward upper end thereof a loading bay for receiving a capped lancet 12/20. The loading bay is closed by a cover 34 which is pivotally and slideably moveable in the housing. Closing the cover and then pushing it rearwardly causes the lancet body 12 to be pulled rearwardly clear of the cap 20 thereby exposing the lancet needle. Further rearward movement of the shifts the lancet cover into a battery position ready to be driven forwardly by a drive mechanism when fired.

18 Claims, 11 Drawing Sheets

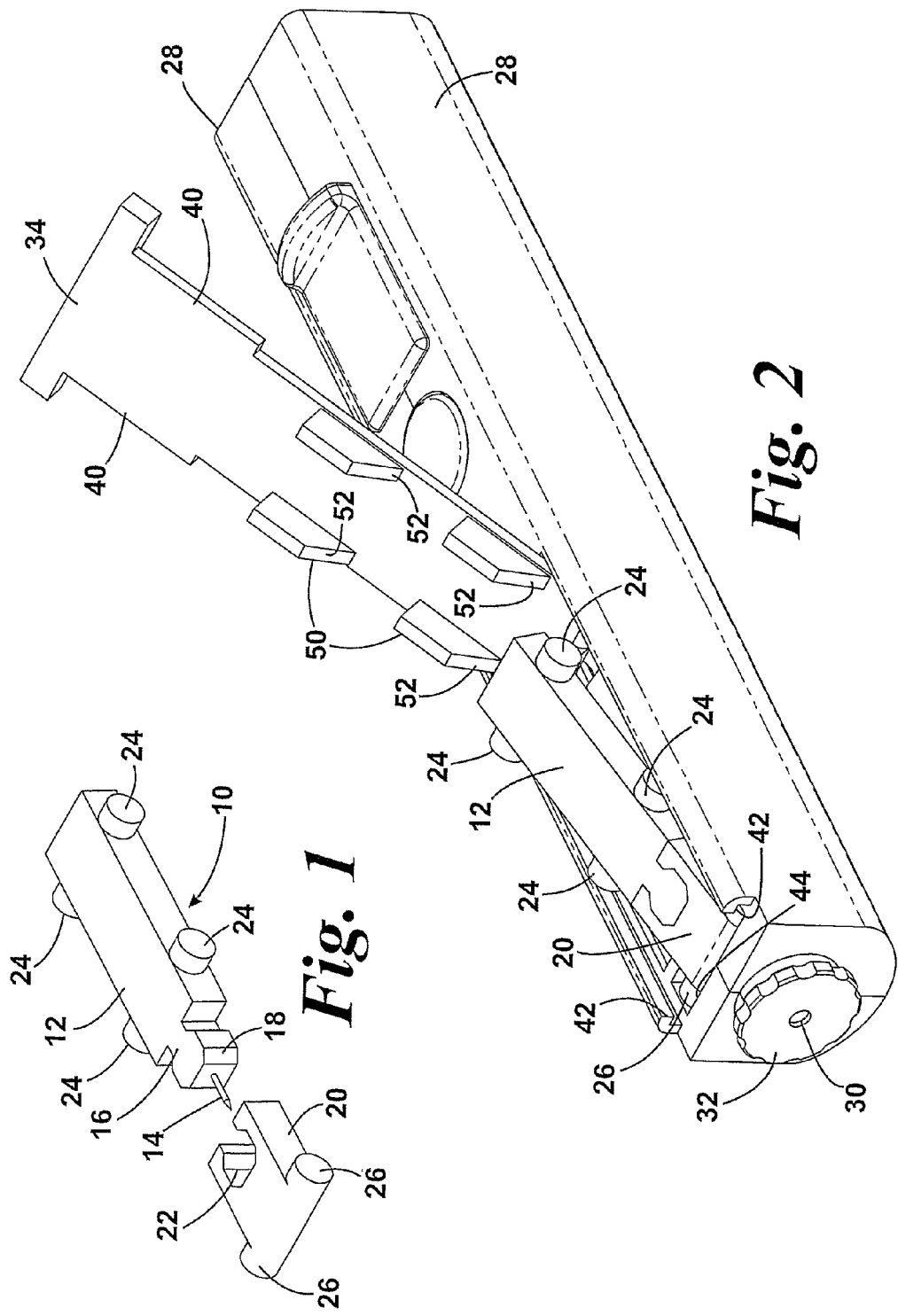

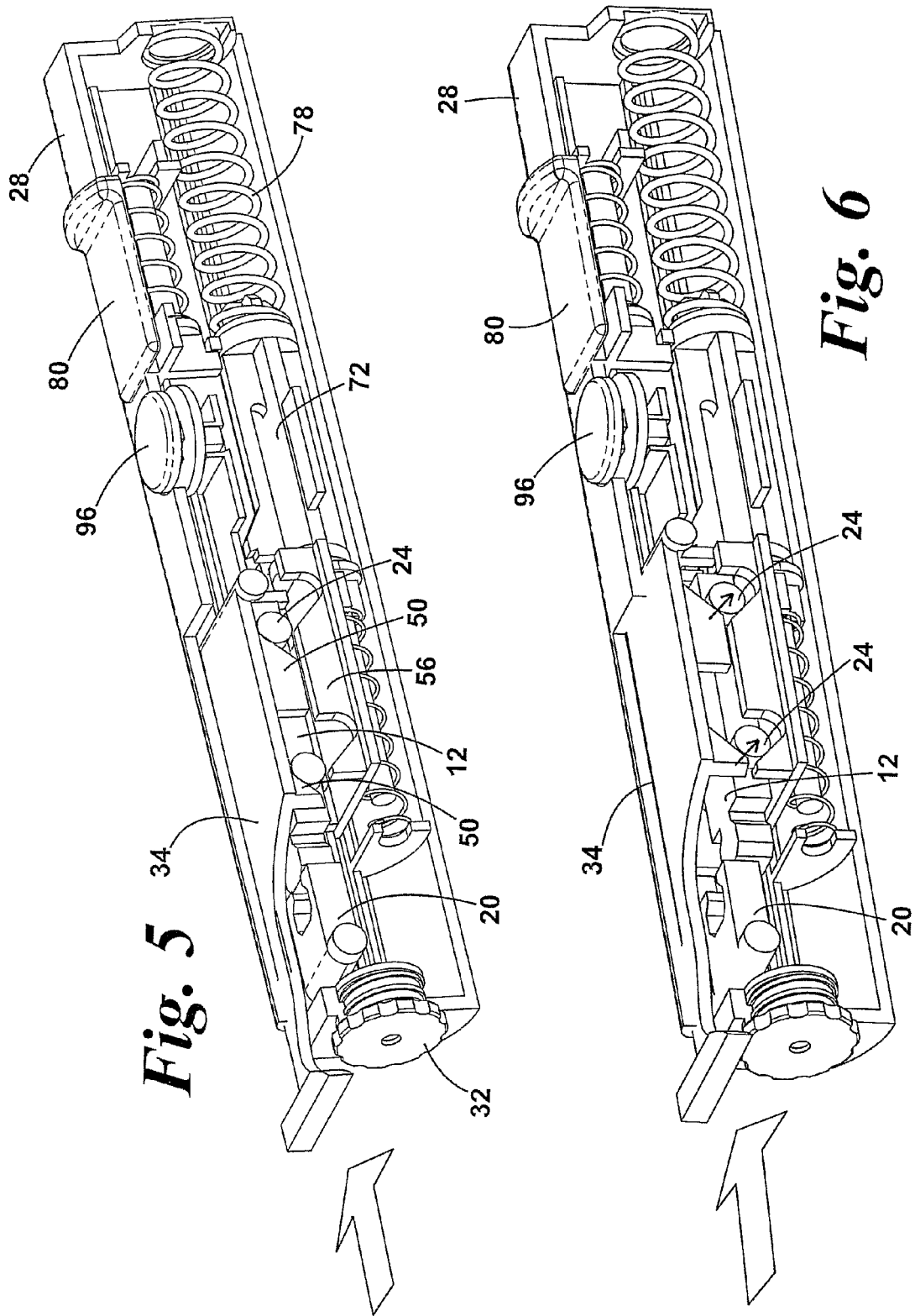

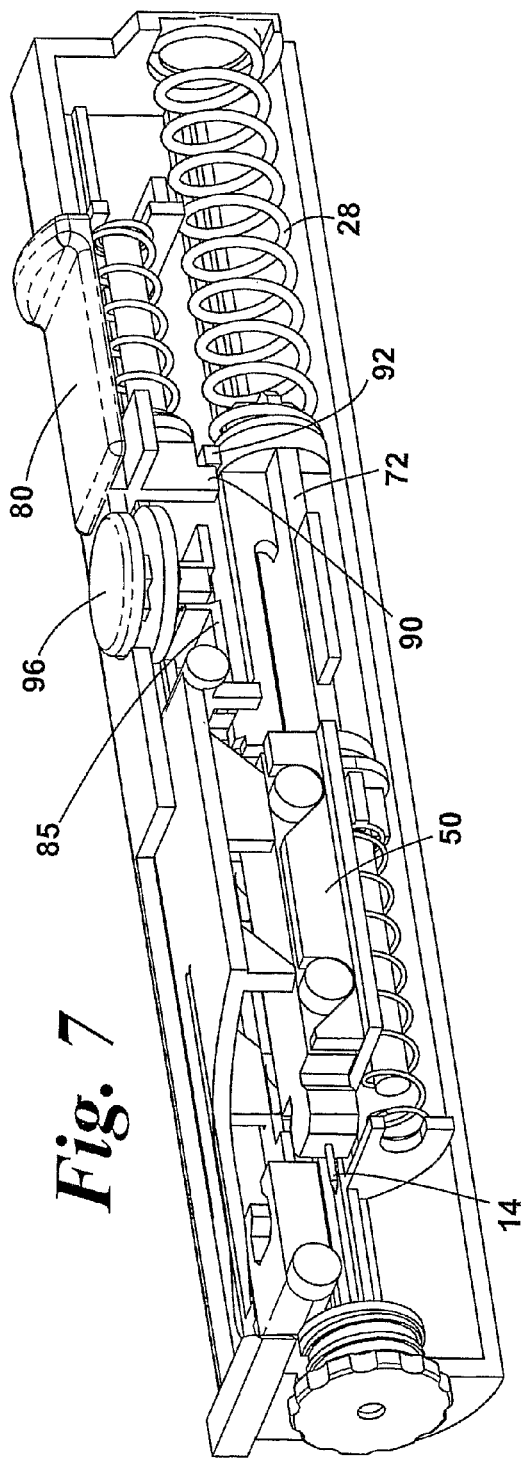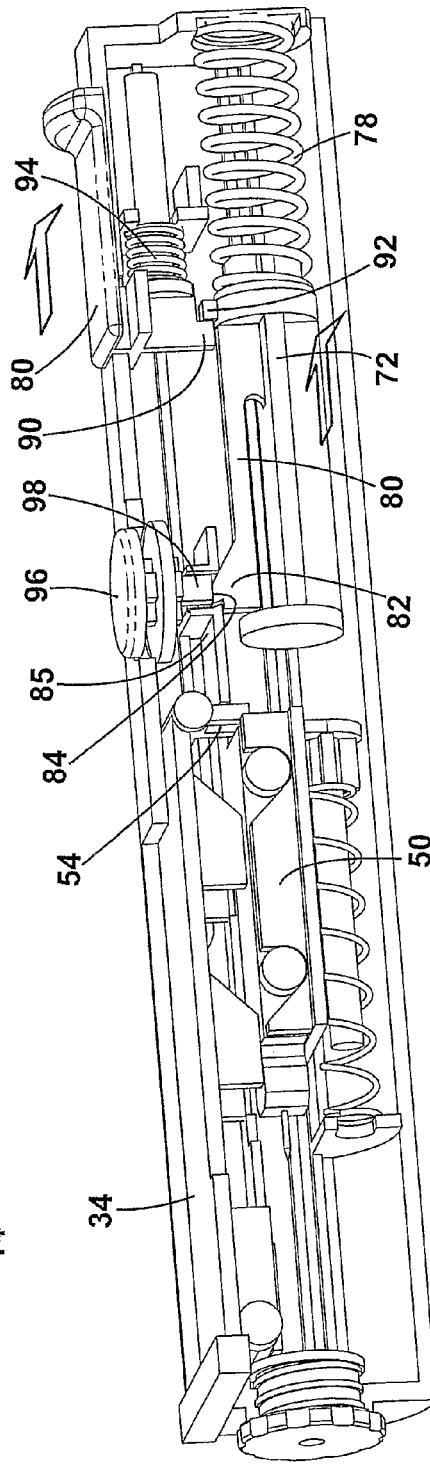

LANCING DEVICES

BACKGROUND OF THE INVENTION

1. Field of the Invention

This invention relates to lancing devices and in particular, but not exclusively, to such devices for use with a disposal lancet having a removable cap.

2. Description of the Related Art

There are many applications where a user needs to draw a bead of blood regularly for test purposes. It is known to provide lancing devices with disposable lancets for this purpose. One conventional form of lancet is provided with a moulded-on cap which keeps the lancet tip sterile and also protects the user when loading the lancet into the device. It is also known to use the same cap to cover the tip of the lancet after use and prior to disposal thereof. In our co-pending application WO2006/128752 we disclose a lancet having a body and a tip and a cap which is bonded to the body by a relatively weak bond so that the cap can be easily slid off the lancet body. This obviates the need for the twisting off action of the previously described type of lancet.

In conventional lancing devices, the lancet is pushed rear end first into the lancet holder within the lancing device with pressure being applied on the front end of the lancet. Although the provision of a moulded-on cap normally shrouds the needle, there is a risk that the pushing action may damage the needle contained under the moulded-on cap or, at worst, the cap may slip off prematurely exposing the lancet tip. Given the small size of lancing devices, the lancet cap can be quite small and therefore awkward for those of reduced dexterity to remove. Accordingly, there is a need for a lancing device in which uncovering of the lancet tip is done automatically, and preferably within the lancing device itself.

SUMMARY OF THE INVENTION

Accordingly, in one aspect, this invention provides a lancing device for receiving in use a lancet having a removable cap, said device including:

a housing;

a loading station adapted to receive in use said lancet;

a drive disposed within said housing and actuable to fire said lancet in use momentarily to project its tip from the device;

an uncapping arrangement for uncapping said lancet in use when in said housing, and a transfer arrangement for moving said lancet in use from said loading station to an in-battery position ready to be fired by said drive.

In the above arrangement a lancet with a removable cap is loaded in use into said loading station and the removable cap is removed by the uncapping means, with the lancet being moved to an in-battery position.

Preferably, said means for uncapping said lancet includes retaining means for retaining said cap relative to said housing, and means for moving said lancet relative to said housing to remove said cap in an uncapping phase of movement.

Preferably, said lancing device includes means for recapping said lancet with said removable cap within said housing after firing.

Preferably, said loading station is at a forward region of said housing, and said uncapping means moves said lancet rearwardly to uncap it.

Preferably, said loading station is offset from the firing axis along which the lancet tip moves when fired, and said uncapping means in use shifts said lancet to align it generally with said firing axis during or after said rearward movement.

Preferably, said uncapping means includes a moveable cover moveable between an open position in which in use said lancet with its removable cap may be inserted into said loading station, and a closed position in which said loading station, and a lancet contained therein, is generally covered.

Preferably, said moveable cover is captive to said housing and mounted for pivotal movement between said open and closed positions. Advantageously, the cover is additionally slideable relative to said housing, the cover when in the closed position being engageable with a lancet in use to transmit longitudinal movement thereto.

In one arrangement, where the lancet includes a lateral drive lug on each side thereof, said cover preferably includes drive surfaces to engage said drive lugs as said cover is slide rearwardly after closing. The cover also conveniently includes an ejection surface adapted in use to lift the rear of a lancet when the cover is open. The cover may be transparent or opaque.

Preferably, said loading station comprises a recess defined within said housing, said recess including guide means for guiding said lancet in use for rearward uncapping movement, and being complimentarily shaped with respect to said lancet such that said lancet is moved towards said firing axis after a pre-set extent of longitudinal movement.

Where the lancet has transverse drive lugs, the housing may conveniently include a guide surface with cut outs to allow passage of said lugs as said lancet moves towards said firing axis.

The device conveniently includes a lancet carriage disposed to receive said lancet in use and to align it with said firing axis, said lancet carriage being moveable against a bias from an equilibrium position in which the lancet tip is within said housing to a projecting position in which the lancet tip projects from said housing.

The drive means may take various forms but may conveniently comprise a hammer mounted for sliding movement within said housing for movement against the bias of a drive spring from an equilibrium position to a latched, cocked position, and trigger means for unlatching said hammer.

In another aspect, this invention provides a lancing device for receiving in use a lancet having a removable cap, said device including:

a housing;

a loading station adapted to receive in use said lancet;

a drive disposed within said housing and actuable to fire said lancet in use momentarily to project its tip from the device, and an arrangement for uncapping said lancet in use when in said housing.

In another aspect, this invention provides a lancet comprising a main body of strip form with a cap, the body and cap having respective drive surfaces for engagement in use by the housing and lancet carriage of a lancing device as described above.

In yet another aspect, this invention provides a lancet having an elongate main body portion, a tip, and a cap portion for covering said tip, at least one of said main body portion and said cap portion having a resilient engagement element for allowing said cap to be removed and reapplied by relative longitudinal movement.

Whilst the invention has been described above, it extends to any inventive combination set out above or in the following description.

BRIEF DESCRIPTION OF THE DRAWING FIGURES

The invention may be performed in various ways, and an embodiment thereof will now be described by way of example only, reference being made to the accompanying drawings, in which FIG. 1 is a view of a disposable lancet with a removable cap for use in the lancing device illustrated in FIGS. 2 to 14;

FIG. 2 is a perspective view of a lancing device of this invention with the lancet in the loading station;

FIGS. 3 to 7 are side views of the lancing device with the right hand housing removed showing the steps of loading a lancet into the loading bay, closing the cover and pushing the cover rearwardly to move the lancet into a loading carriage;

FIGS. 8 and 9 are side views with the left hand housing half removed showing cocking of the device and firing respectively;

DETAILED DESCRIPTION OF THE INVENTION

Figure 3:
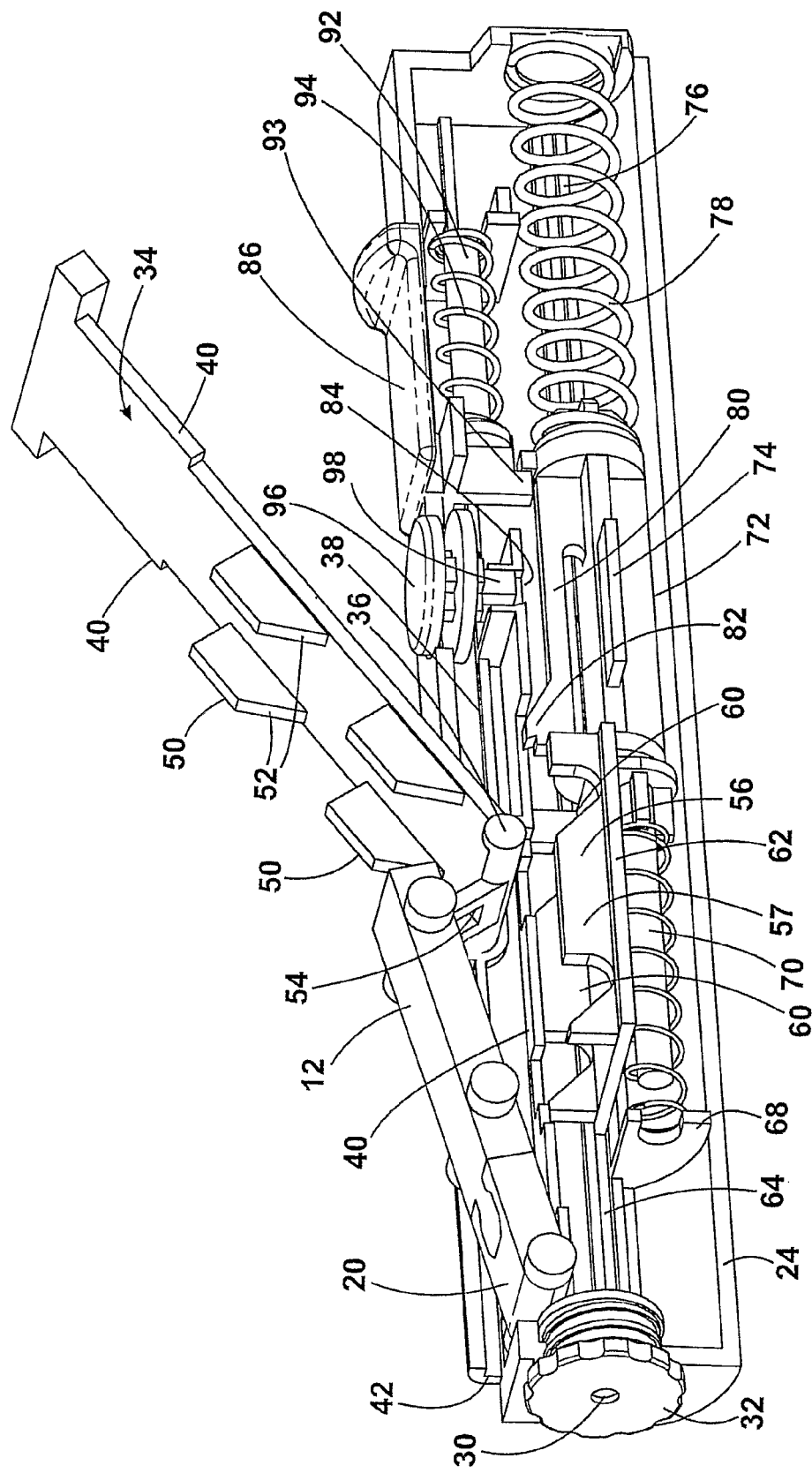
Figure 4:
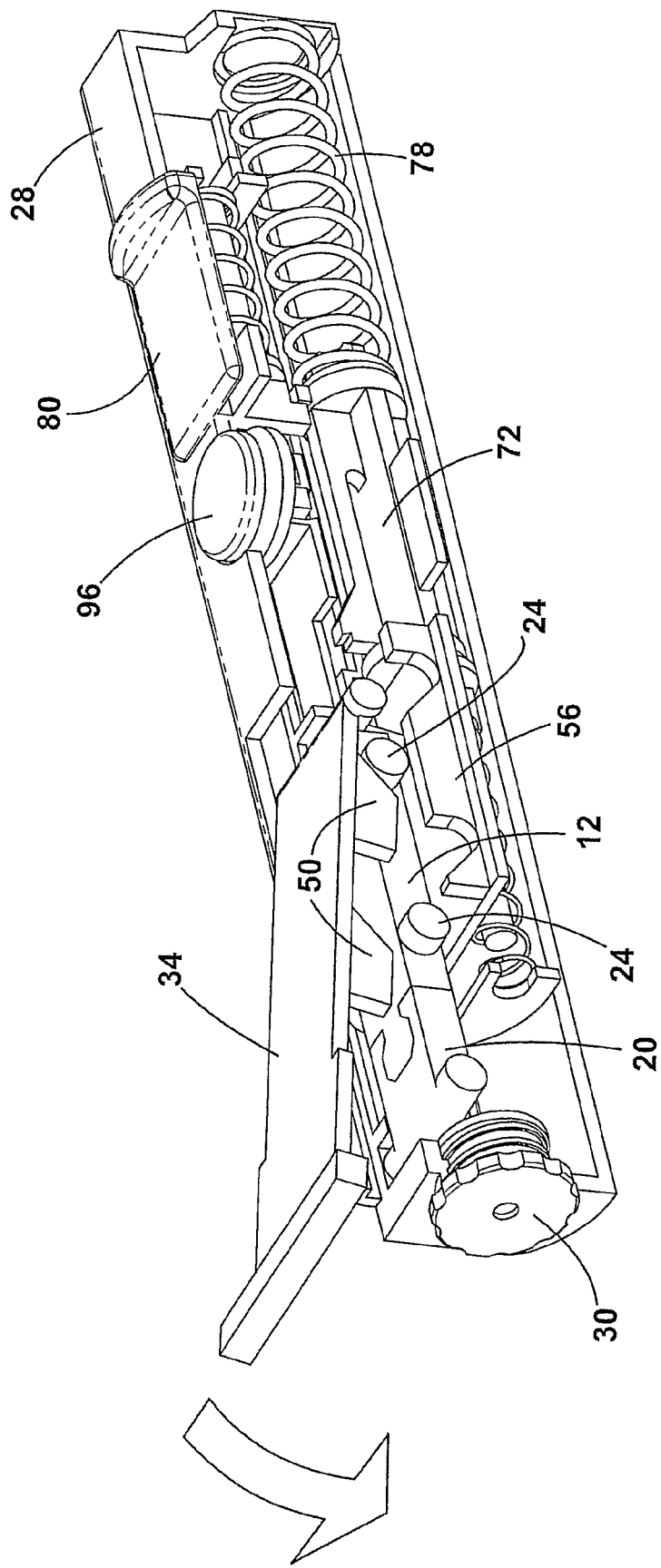
Figure 9:
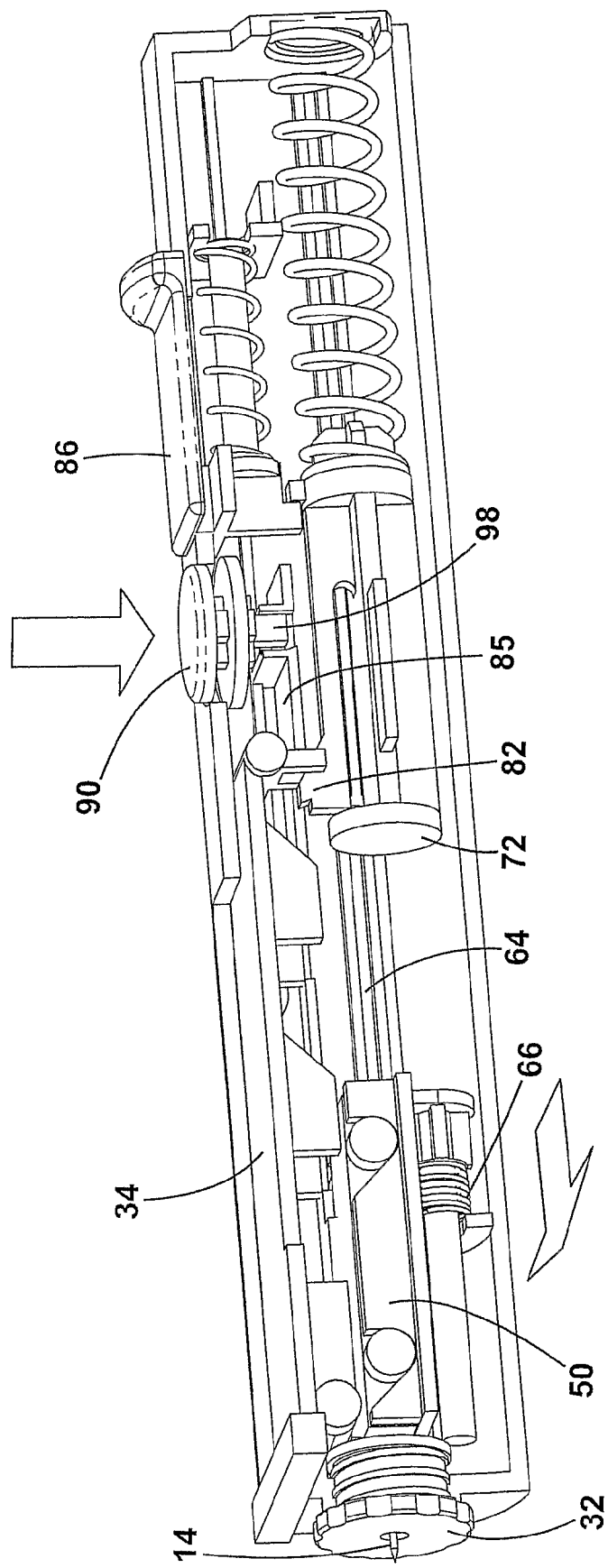

Referring initially to FIG. 1 there is shown first form of re-cappable lancet in accordance with an aspect of the invention. The lancet 10 has a main body 12 of generally rectangular strip form encasing a needle whose tip 14 projects from the forward end of the lancet. The front end of the body is necked at 16 to provide an enlarged head 18. A cap 20 of similar flat rectangular section has a capping recess 22 designed to snap around the head 18 of the main body. The main body 12 has two pairs of laterally extending drive lugs 24, and the cap 20 has a pair of similarly dimensioned transverse cap lugs 26. The cap 20 and the lancet body 12 are designed so that the cap shields a tip and provides a sterile shield for the tip prior to use, the cap being removable and replaceable by pulling it off or pushing it on to the main body longitudinally. The cap and lancet can be produced by a twin shot moulding process whereby a lancet body is injection moulded about the needle leaving the tip protruding from the body and a cap is then overmoulded about the tip of the needle as set out in our published application WO2007/085865.

Referring now to FIG. 2, the illustrated embodiment of lancing device comprises a main housing made up of two housing halves 28 which contains the drive and trigger mechanism for the lancet which is designed to be driven momentarily to project through the aperture 30 of a nose piece 32 which is threaded into the forward end of the housing to allow axial adjustment of the nose piece and thus the pre-set penetration depth.

Figure 12:
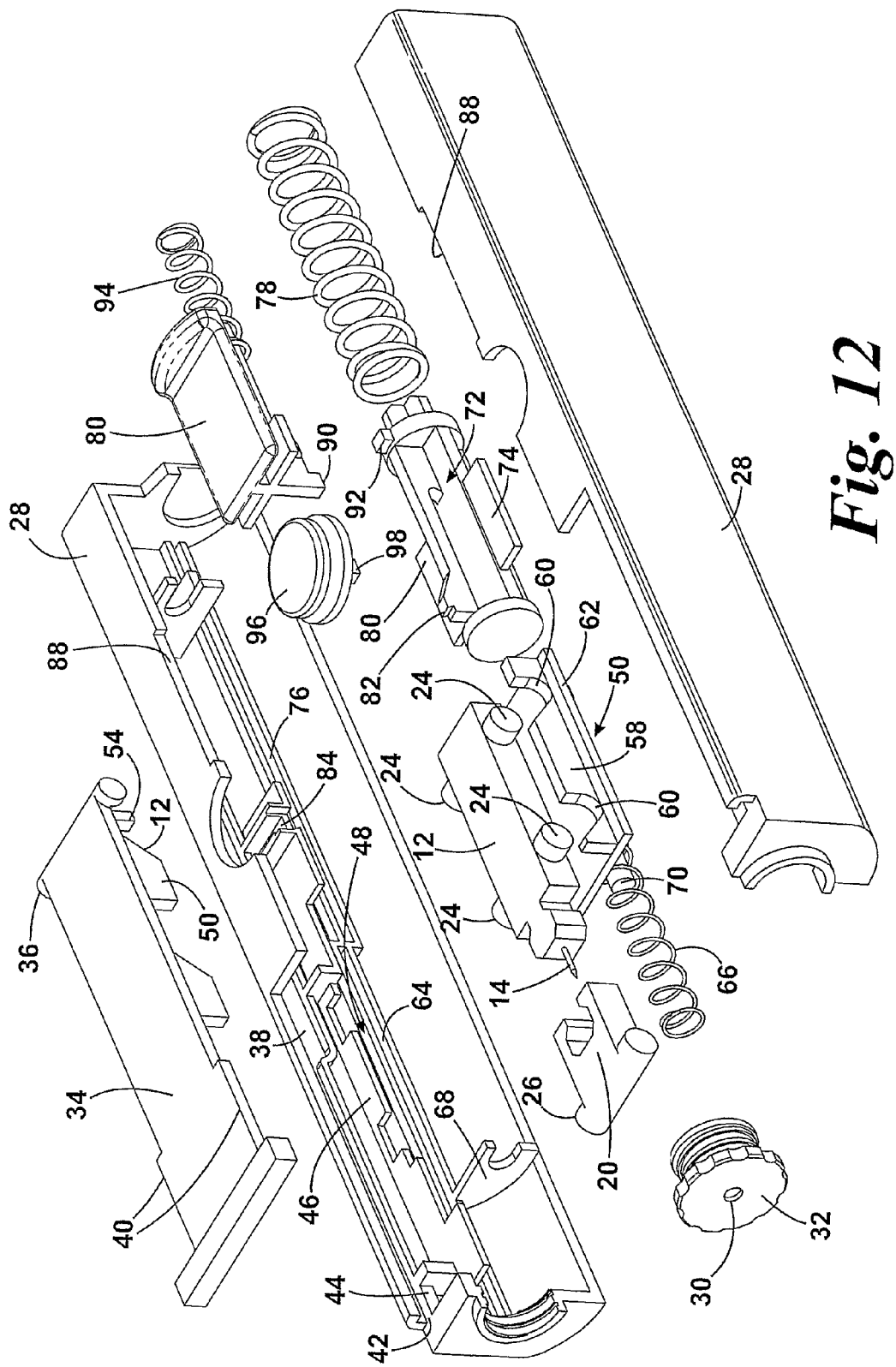
FIG. 12 is an exploded view of the lancing device and the lancet.
Figure 13:
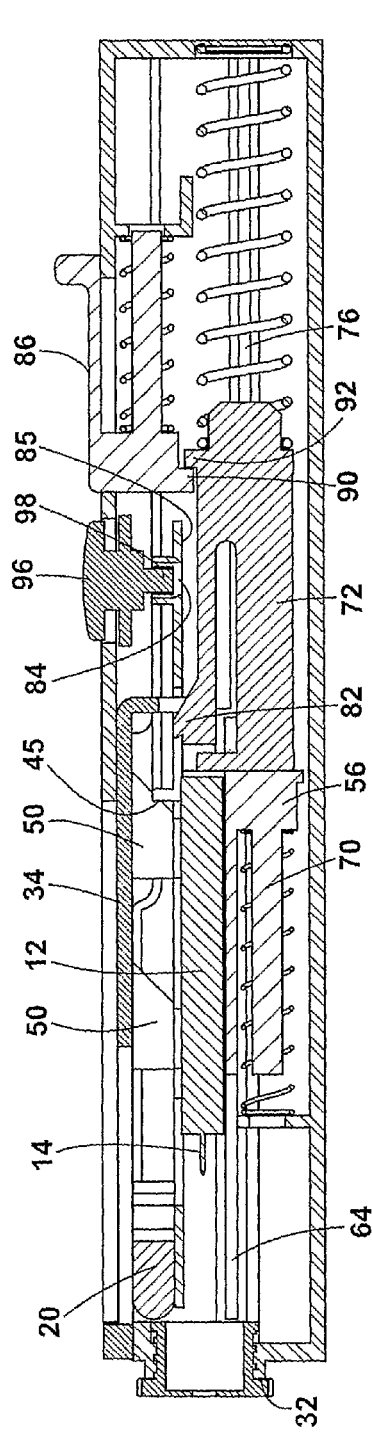
FIG. 13 is a side section view.
Figure 14:
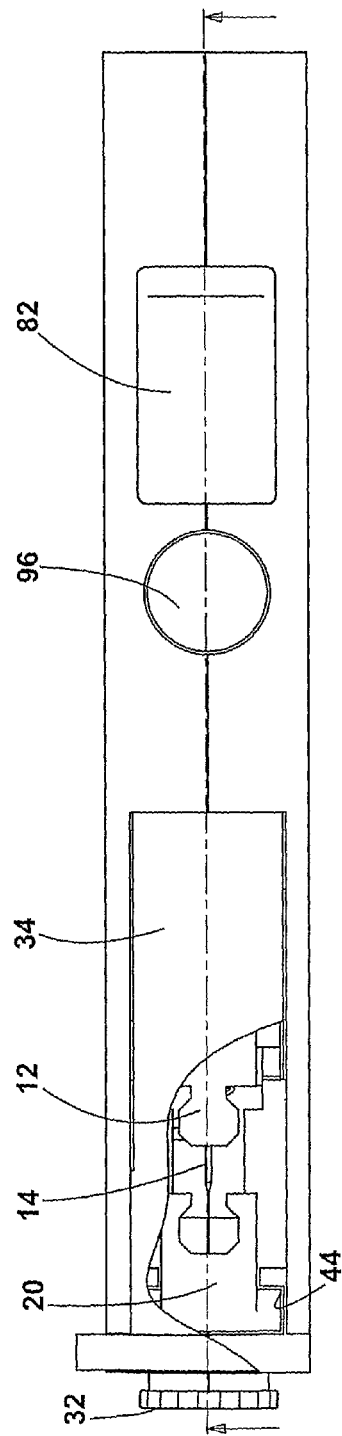
FIG. 14 is a top plan view with part of the cover removed for clarity.

A transparent cover 34 is captive to the forward upper end of the housing by hinge lugs on the cover running in respective hinge guides 38 on the inner wall of each housing half 28 (see e.g. FIG. 12). The cover 34 is moveable between the open position shown in FIGS. 2 and 3 to a folded forward position in which it lies generally parallel with the upper surface of the casing, as shown in FIG. 5. From here the cover 34 can be pushed rearwardly such that locking ribs 40 engage and slide into locking slots 42 on the housing.

When open, the cover 34 reveals the loading station area within the forward end of the lancing device, into which a lancet may be loaded as in FIG. 2. When first loaded into the loading station, the lugs 26 of the cap 20 are received in capture recesses 44 formed in the inner walls of the casing halves 28. The lancet body 12 is supported on a false floor 46 defined by opposed wall sections projecting inwardly of the housing halves 28. The false floor 46 has a cutaway region 48 through which the lancet 10 may be urged downwardly when it is shifted rearwardly from the loading position as to be described in more detail below.

Figure 10:
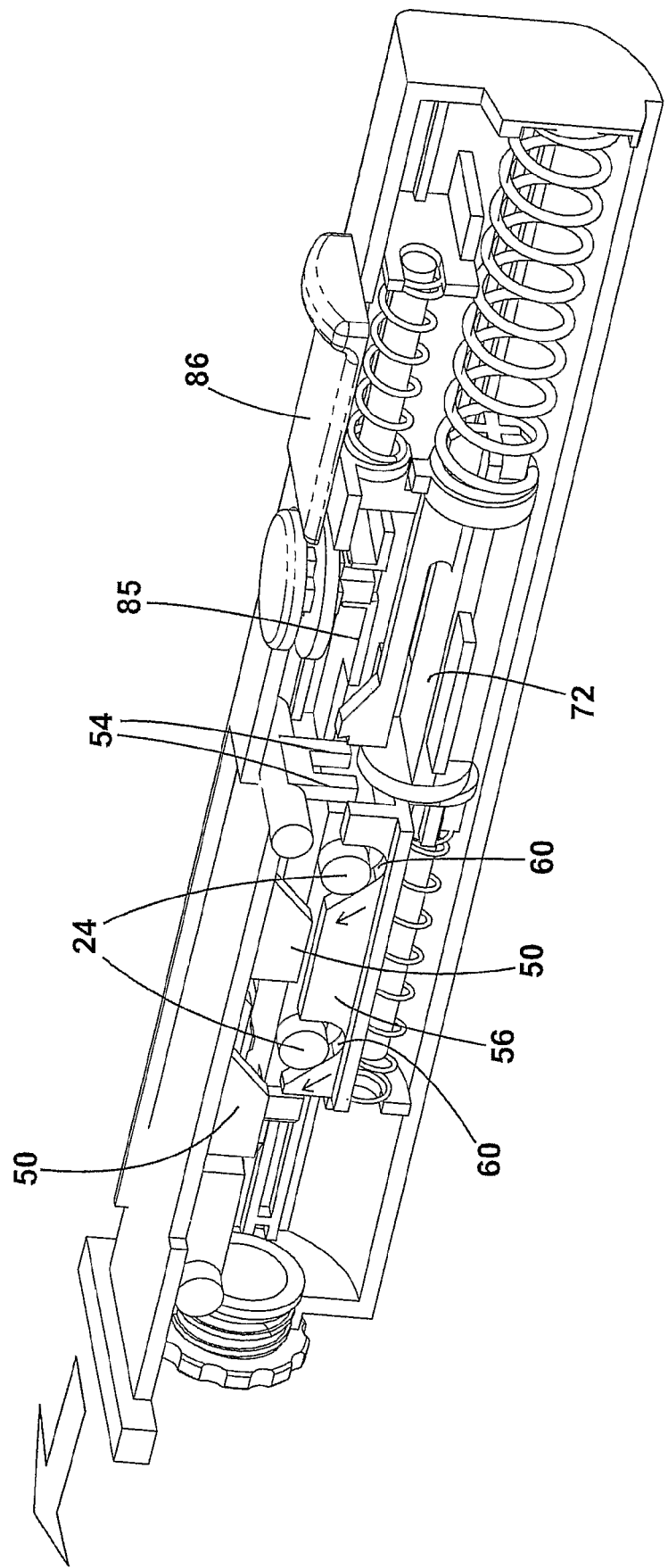
FIGS. 10 and 11 show the device when the cover is shifted forwardly to move the used lancet out of the lancet carriage back to the loading station.
Figure 11:
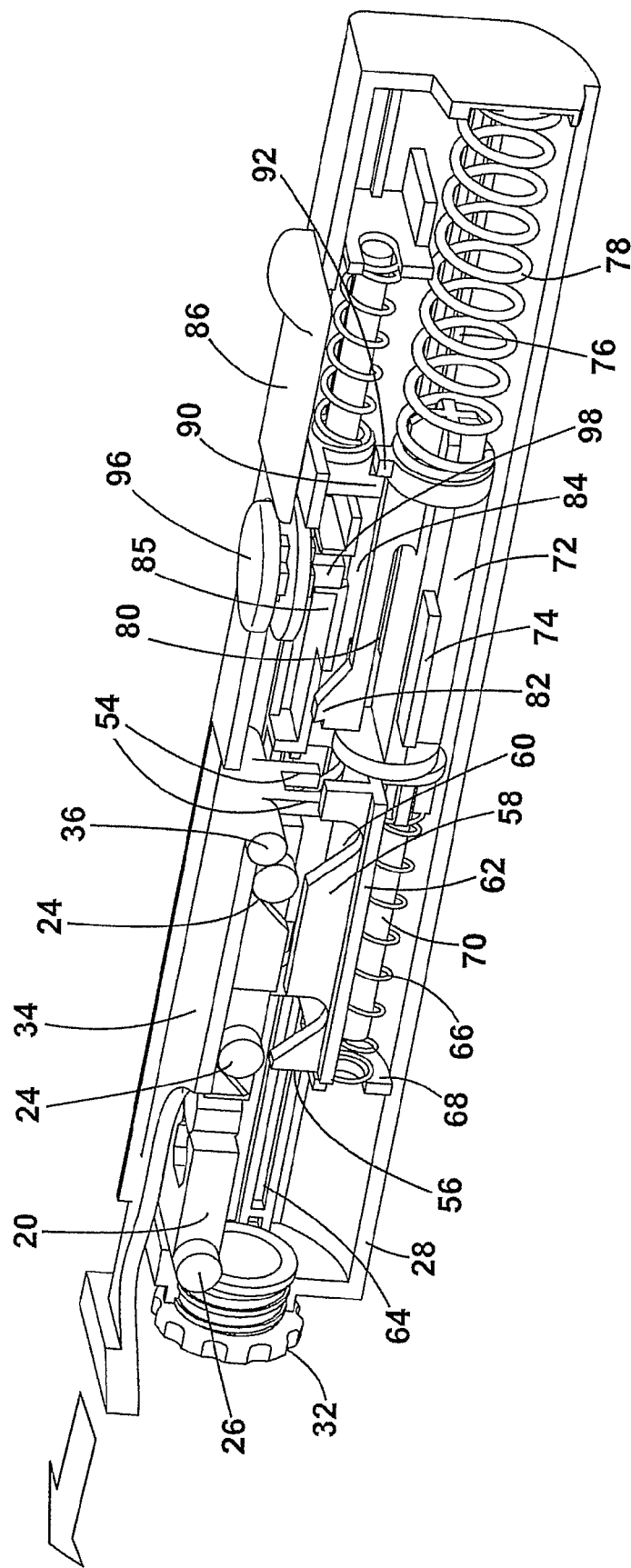

The cover 34 has four trapezoidal shaped guide lugs 50 that have on their rearward surfaces inclined drive faces 52 for engaging the drive lugs 24 on the lancet main body 12. The cover 34 also has a pair of ejector fingers 54 extending transversely from the axis of the hinge lug which can be seen more clearly in FIGS. 10 and 12. When the cover 34 is opened, the ejector fingers upstand from the false floor of the loading station to lift the rear end of the lancet 12 clear of the housing 28.

Located beneath the false floor 46 and generally aligned under the cutaway region 48 is a lancet carriage 56 having a cradle region for receiving the lancet 12 comprising side walls 58 with four slots 60 for receiving the drive lugs 24 of the lancet. The slots 60 have ramped forward surfaces for assisting engagement and disengagement of the lancet with the carriage 56.

The lancet carriage 56 is slideably mounted for longitudinal movement within the casing 28 by means of transverse ribs 62 on each side thereof which engage in respective slots 64 on the interior of the housing halves 28. The lancet carriage determines the path of the lancet tip 14 (otherwise referred to herein as the firing axis). The lancet carriage is biased rearwardly by means of a compression spring 66 which engages an interior wall 68 of the casing 28 at one end and the base of a spring support stem 70 on the lancet carriage at its other end. The forward and rearward extents of the movement of the carriage 56 are determined by the axial extent of the slots 64.

To the rear of the lancet carriage 56 is a hammer 72 which has lateral ribs 74 which slide in respective slots 76 on the inner walls of the housing 28. The hammer 72 is urged forwardly by a strong drive spring 78 acting between the rear end of the hammer and the inner rear wall of the housing 28. It will be noted that the drive spring 70 is stronger than the carriage spring 66 so that, in the rest position shown in FIGS. 2 to 7, the hammer is at its forward most position, urging the lancet carriage 56 a little forward of its rearmost position. On its upper surface, the hammer 72 has a forwardly extending resilient latching arm 80 with a latch piece 82 designed to be latched into a latch through-hole 84 formed in an inner wall 85 of the housing, when the hammer is cocked.

The hammer is cocked or loaded by means of an externally projecting slider 86 which projects through a slot 88 in the housing and has a forward, downwardly directed tooth 90 that cooperates with a drive rib 92 on the rear end of the hammer 72. The slide 80 is biased forwardly by a compression spring 94.

An externally accessible trigger button 96 is captive to the upper wall of the housing and has a trigger stem 98 that engages the latch through-hole 84. When the hammer is latched with the latch piece 82 in the through-hole, pressing the trigger button 96 causes the stem to push the latch piece 82 clear of the latch through-hole so the hammer 72 shoots forwardly to impact the rear of the lancet holder 56 to drive it, and the uncapped lancet 12, forwardly to cause the lancet tip 14 to project through the nose piece 32.

In use, assuming the device is initially empty, it is made ready for loading by sliding the transparent cover 34 forwardly and flipping it open. A lancet with cap attached is then placed in the loading station, locating the capture lugs 26 on the lancet cap in the capture recesses 44 in the casing, and with the rear of the lancet 12 resting on the ejection teeth 50 (FIGS. 2 and 3). The transparent cover 34 is then hinged forwardly (FIG. 4) to the position shown in FIG. 5, where the cover is parallel to the top of the casing with the guide lugs contacting the forward surfaces of the drive lugs of the lancet body. The cover is then pushed rearwardly so that the locating ribs 40 on the sides thereof locate and slide in the locking groove 42 in the housing. As this is happening, the guide lugs 50 engage the drive lugs 24 on the lancet to shift it rearwardly along the false floor 46 to uncap it, with the rear end of the lancet the main body 12 coming to rest against an internal wall 45. With further rearward movement in this plane prevented, the continued rearward movement of the cover 34 causes the drive surfaces 52 to cooperate with the drive lugs 24 on the lancet body to push it downwardly through the cutaway region so that the lugs 24 engage the slots 60 and ride down the ramp surfaces thereof so that the lancet portion is cradled by the lancet carriage 58 (FIGS. 6 and 7).

The hammer is then cocked by sliding the slider 86 rearwardly which pulls the hammer 72 rearwardly by co-engagement of the drive teeth 90, 92, until the latch piece 82 engages in the latch through-hole 84 thereby cocking the device. This slide is released to return to its original position (FIG. 8).

When the user is ready, and the device positioned against the skin, the button 96 is pressed which unlatches the latch piece 82 from the through-hole 84 so that the hammer 72 shoots forwardly, to impact the rear of the lancet carriage 56 which travels forwardly to project the lancet tip 13 through the nose piece 30, compressing the lancet carriage spring 66. The lancet carriage is then immediately returned to its equilibrium position by the spring 66.

After firing, the transparent cover 34 is slid forwardly so that the ejection fingers 54 pull the lancet main body portion clear of the lancet carriage, back through cutaway region 48 hence to move along the false floor 46 to re-engage the lancet with the cap so that the cap clips back onto the lancet into place. The cover is then flipped over and the ejection fingers 54 lift the rear end of the lancet clear of the housing.

Figure 15:
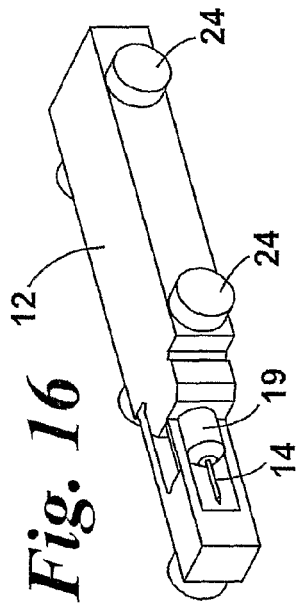
FIGS. 15, 16, 17a and 17b are views of an alternative form of a disposable lancet with a removable cap for use in this invention.
Figure 16:
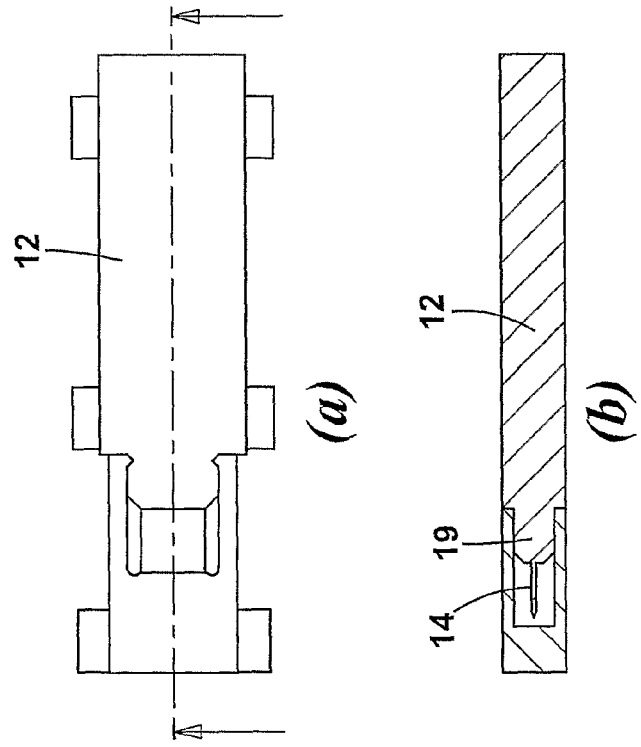
Figure 17:
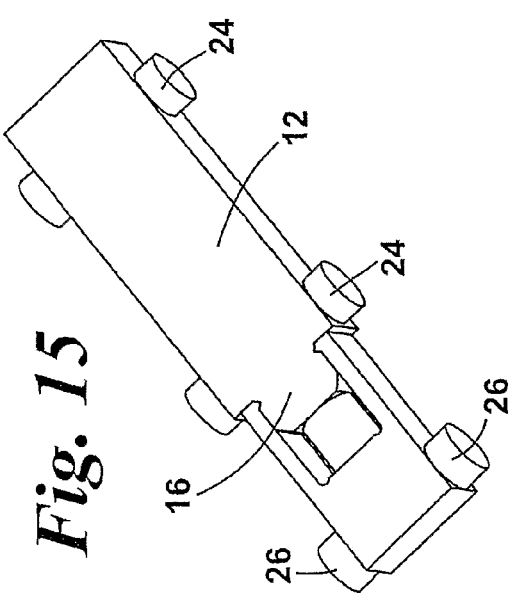

Referring now to FIGS. 15 to 17, there is shown another embodiment of the lancet for use in this invention. The lancet's main body portion is of similar design to that shown in FIG. 1. In this embodiment, the cap is separate, and modified to safeguard sterility of the tip and to make re-capping of the lancet easier. The lancet body is modified so that it defines a short cylindrical portion 19 at the top of the head where the tip exits 14. The lancet cap 20 is provided with a cylindrical shell part 21 which fits over the cylindrical portion 19. The cap also is retained by means of rearwardly extending arms 23 which snap fit around the neck.

The invention claimed is:

1. A lancing device for receiving in use a lancet having a removable cap, said device including:
   a housing;
   a loading station adapted to receive in use said lancet;
   a drive disposed within said housing and actuable to fire said lancet in use momentarily to project a tip of the lancet from the device;
   an uncapping arrangement for uncapping said lancet in use when in said housing;
   a transfer arrangement for moving said lancet in use from said loading station to a firing position, ready to be fired by said drive; and
   a cover associated with said loading station and which is rotatable between an open and a closed position, the cover being additionally slideable relative to said housing, at least when closed and, when in the closed position, being operable in use to transmit longitudinal movement to the lancet in said loading station,
   wherein said cover in use is movable before the lancet has been fired to move said lancet longitudinally to remove said cap, and is movable after the lancet has been fired to move said lancet longitudinally into reengagement with said cap to recap the lancet.

2. The lancing device according to claim 1, wherein said uncapping arrangement includes a retaining arrangement for retaining said cap relative to said housing.

3. The lancing device according to claim 2, wherein said loading station is at a forward end of said housing, and said lancet is moved rearwardly to uncap the lancet.

4. The lancing device according to claim 3, wherein said loading station is offset from the firing axis along which the lancet tip moves when fired, and said lancet is shifted in use to align the lancet generally with said firing axis, during or after said rearward movement.

5. The lancing device according to claim 4, which further includes a lancing carriage disposed to receive said lancet in use, and to align it with said firing axis, said lancet carriage being movable against a bias from an equilibrium position in which the lancet tip is within said housing, to a projected position in which the lancet tip projects from said housing.

6. The lancing device according to claim 1, wherein in the open position of said cover use a the lancet with a removable cap may be inserted in said housing, and in the closed position of said cover said loading station, and a lancet therein, is generally covered.

7. The lancing device according to claim 1, wherein said moveable cover is captive to said housing and is mounted for pivotal movement between said open and closed positions.

8. The lancing device according to claim 1, wherein said cover is closed, the cover is engageable with the lancet in use to transmit longitudinal movement thereto.

9. The lancing device according to claim 1, wherein said lancet includes two lateral drive lugs and said cover includes drive surfaces to engage said drive lugs.

10. The lancing device according to claim 1, wherein said cover includes ejection abutment surfaces designed to lift a rear of the lancet in the unloading station when said cover is open.

11. The lancing device according to claim 1, wherein said cover is transparent.

12. The lancing device according to claim 1, wherein said loading station comprises a recess within said housing, said housing including means for guiding said lancet in use for rearward uncapping movement, and being complementarily shaped with respect to said lancet such that said lancet is capable of moving transversely towards said firing axis after a predetermined extent of rearward longitudinal movement.

13. The lancing device according to claim 12, wherein said lancet has transverse lugs, and said housing includes a guide surface with one or more cut outs to allow passage of said lugs.

14. The lancing device according to claim 1, wherein said drive comprises a hammer mounted for sliding movement within said housing against a bias of a drive spring from an equilibrium position to a cocked position, and a trigger for unlatching said hammer from a cocked position.

15. The lancing device according to claim 1, in combination with the lancet comprising a main body (12) of flat strip form with a cap, the body and cap having respective drive surfaces for engagement in use by the housing and a lancet carriage in said lancing device.

16. The lancing device according to claim 1, in combination with the lancet having an elongate main body portion, a tip and a cap portion for covering said tip, at least one of said main body portion and said cap portion having a resilient engagement portion for allowing said cap to be removed and reapplied by relative longitudinal movement.

17. The lancing device according to claim 16, wherein one of said cap and said main body have a male engagement portion and the other has a female engagement portion, the male and female portions being engaged and disengaged by snap action.

18. The lancing device according to claim 17, wherein said main body portion has a necked male head region and said cap includes a female recess.

\* \* \* \* \*

UNITED STATES PATENT AND TRADEMARK OFFICE
CERTIFICATE OF CORRECTION

PATENT NO. : 8,460,330 B2  Page 1 of 1
APPLICATION NO. : 12/673364
DATED : June 11, 2013
INVENTOR(S) : Nicholls et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 248 days.

Signed and Sealed this
Eighth Day of September, 2015

Michelle K. Lee
*Director of the United States Patent and Trademark Office*